United States Patent [19]

Dreckmann et al.

[11] Patent Number: 4,970,077
[45] Date of Patent: Nov. 13, 1990

[54] NEW 6-SUBSTITUTED-4-HYDROXTETRAHYDRO-PYRAN-2-ONE DERIVATIVES AND PHARMACEUTICAL COMPOSITIONS CONTAINING THEM

[75] Inventors: Bruno Dreckmann, Mannheim; Reinhard Heck, Oftersheim; Johannes Pill, Leimen, all of Fed. Rep. of Germany

[73] Assignee: Boehringer Mannheim GmbH, Mannheim, Fed. Rep. of Germany

[21] Appl. No.: 358,792

[22] Filed: Jun. 1, 1989

[30] Foreign Application Priority Data

Jun. 1, 1988 [DE] Fed. Rep. of Germany ....... 3818570

[51] Int. Cl.$^5$ .................... A61K 9/20; A61K 31/365; C07D 309/30
[52] U.S. Cl. .................................. 424/464; 514/460; 549/292
[58] Field of Search ...................... 549/292; 424/464; 514/460

[56] References Cited

FOREIGN PATENT DOCUMENTS 0232997 8/1987 European Pat. Off. .
0344602 12/1989 European Pat. Off. .
3530797 3/1987 Fed. Rep. of Germany .

Primary Examiner—Richard L. Raymond
Assistant Examiner—A. A. Owens
Attorney, Agent, or Firm—Armstrong, Nikaido, Marmelstein, Kubovcik & Murray

[57] ABSTRACT

The present invention provides compounds of the general formula:

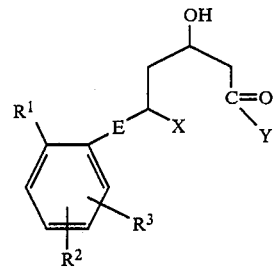

wherein E is an alkylene or alkenylene radical containing 2 carbon atoms, $R^1$ is a cycloaliphatic hydrocarbon radical containing 5 to 12 carbon atoms, which is optionally substituted by up to 4 lower alkyl radicals, as well as halogen atoms, and can optionally be mono- or polyunsaturated, $R^2$ and $R^3$, which can be the same or different, are further cycloaliphatic hydrocarbon radicals containing 3 to 7 carbon atoms, hydrogen or halogen atoms, trifluoromethyl radicals or alkyl or alkoxy radicals containing up to 7 carbon atoms which can optionally also be substituted with methyl radicals, X is hydroxyl, Y is a residue of an alcohol or a residue of an amine or the group OZ, Z is hydrogen, an alkali metal or ammonium ion or X and Y taken together are —O—. Thus, these compounds are lactones or hydroxy acids of the formulae:

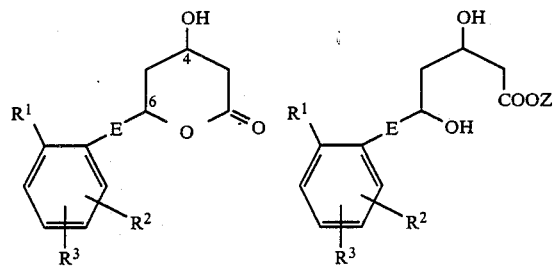

wherein E, $R^1$, $R^2$ and $R^3$ are as stated above, and Z is a hydrogen atom, and alkali metal ion or an ammonium ion; the esters and amides of the free carboxylic acids and the stereoisomeric forms thereof.

The present invention also provides processes for the preparation of these compounds and pharmaceutical compositions containing them.

21 Claims, No Drawings

NEW 6-SUBSTITUTED-4-HYDROXTETRAHYDROPYRAN-2-ONE DERIVATIVES AND PHARMACEUTICAL COMPOSITIONS CONTAINING THEM

The present invention is concerned with new 6-substituted-4-hydroxytetrahydropyran-2-one derivatives, processes for the preparation thereof and pharmaceutical compositions containing them.

The main risk factor for atherosclerotic changes of the coronary arteries with heart infarct as a result is an increased concentration of cholesterol-containing lipoproteins of low density (LDL, low density lipoproteins) in the plasma. Therefore, the lowering of the cholesterol level serves not only for prophylaxis but also for therapy in this multifactor disease (Lipid Research Clinics Program, LRC-CPPT, J. Am. Med. Assos., 251, 351-375/1984).

Since a large part of the cholesterol is to be attributed to de vovo synthesis, the control of the endogenic cholesterol formation represents an effective therapeutic possibility.

The rate-determining key enzyme for the biosynthesis is 3-hydroxy-3-methylglutaryl-CoA reductase (HMG-CoA reductase). This enzyme is responsible for the regulation of the synthesis of cholesterol. High cholesterol concentrations lower the biosynthesis of HMG-CoA reductase and low intracellular concentrations induce the formation of the enzyme and thus the biosynthesis of cholesterol.

Natural fermentation products from moulds, such as compactin A=(A. Endo et al., J. Antibiot., 29, 1346/1976) and mevinolin (A. W. Alberts et al., J. Proc. Natl. Acad. Sci. USA, 77.395/1980) are able competitively to inhibit HMG-CoA reductase.

In the meantime, numerous synthetic derivatives of this class of active materials, which possess an identical lactone ring, have been described as enzyme inhibitors, for example by G. E. Stokker et al., J. Med. Chem., 28, 347/1985).

The present invention is concerned with new synthetic analogues of 3,5-dihydroxypentanoic acid having the structural formula:

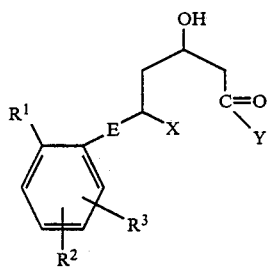

wherein E is an alkylene or alkenylene radical containing 2 carbon atoms, $R^1$ is a cycloaliphatic hydrocarbon radical containing 5 to 12 carbon atoms, which is optionally substituted by up to 4 lower alkyl radicals, as well as halogen atoms, and can optionally be unsaturated one or more times, $R^2$ and $R^3$, which can be the same or different, are further cycloaliphatic hydrocarbon radicals containing 3 to 7 carbon atoms, hydrogen or halogen atoms, trifluoromethyl radicals or alkyl or alkoxy radicals containing up to 7 carbon atoms, which can optionally also be substituted by methyl radicals, X is hydroxyl and Y is a residue of an alcohol or a residue of an amine or the group OZ, Z is hydrogen, an alkali metal or ammonium ion or X and Y taken together are —O—. Thus, the compounds of this invention are in the form of the δ-lactones (Ia) and of the corresponding dihydroxycarboxylic acid derivatives (Ib):

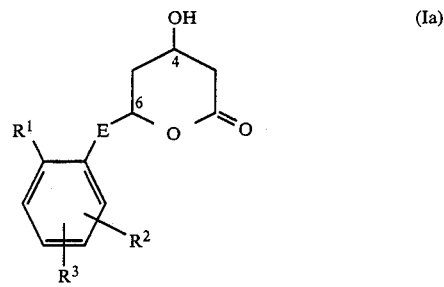

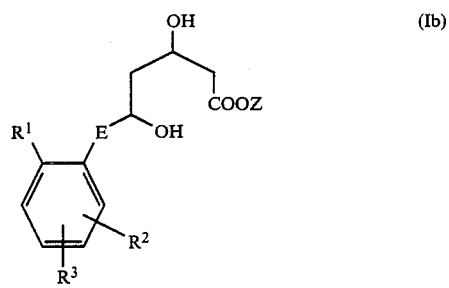

wherein E, $R^1$, $R^2$ and $R^3$ are as set forth above, and Z is a hydrogen atom, an alkali metal ion or ammonium ion, or the esters and amides of the carboxylic acids. All stereoisomeric forms of these compounds are included herein.

Especially preferred compounds according to the present invention are those in which the bridge E is a —CH$_2$CH$_2$— or —CH=CH— radical and especially a —CH=CH— radical.

$R^2$ and $R^3$ are preferably hydrogen or haloqen atoms, trifluoromethyl radicals or alkyl or alkoxy radicals containing up to 4 carbon atoms.

$R^1$ is preferably a cycloalkyl or cycloalkenyl radical containing 5 to 12 carbon atoms.

In the corresponding hydroxycarboxylic acids (Ib), Z is preferably a hydrogen atom, an alkali metal ion, an ammonium ion or an alkyl radical derived from a lower alcohol, for example methanol, ethanol or isopropanol, or also from a polyhydroxy alcohol, for example, glycerol, or is an amino group derived, for example from ammonia, p-aminobenzoic acid, β-alanin, ethanolamine or 2-aminopropanol.

Cycloaliphatic hydrocarbon radicals of the substituent $R^1$ are preferably cyclopentyl, cyclohexyl, cycloheptyl, cyclododecyl, cyclopentenyl, cyclohexenyl, cycloheptenyl or cyclododecenyl radicals.

Cycloaliphatic hydrocarbon radicals of the substituents $R^2$ and $R^3$ are preferably cyclopropyl, cyclopentyl or cyclohexyl radicals.

Lower alkyl radicals are usually radicals containing up to 6 carbon atoms and especially up to 4 carbon atoms, for example methyl, ethyl, or propyl radicals.

The alkyl radicals of the substituents $R^2$ and $R^3$ are preferably methyl, ethyl, propyl or butyl radicals and the alkoxy radicals are preferably methoxy or ethoxy radicals.

By halogen substituents are to be understood, in all cases, fluorine, chlorine or bromine and especially chlorine.

The above definitions of the compounds according to the present invention include all possible stereoisomers, as well as mixtures thereof, preferably the "trans-lactone ring" stereoisomers with the absolute configuration 4R,6S; that corresponds to the absolute configuration 3R,5S in the open-chained dihydroxycarboxylic acid derivatives Ib.

The preparation of the compounds (Ia) and (Ib) is characterised in that an appropriately substituted cinnamaldehyde derivative of the general formula (II):

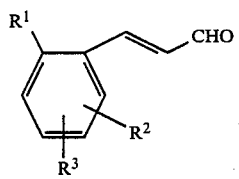
(II)

1. in which $R^1$, $R^2$ and $R^3$ have the above-given meanings and the —CH=CH— radical corresponds to E, is added to the dianion of an acetoacetic acid ester of the general formula:

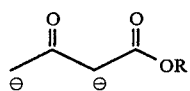
(III)

in which R is a lower alkyl radical, to give a 3-ketocarboxylic acid of the general formula:

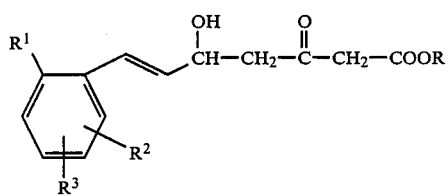
(IV)

in which R, $R^1$, $R^2$ and $R^3$ have the above-given meanings.

The keto function in the compound of general formula (IV) is reduced with a mild reducing agent, for example sodium borohydride, to give a 3,5-dihydroxycarboxylic acid ester of the general formula:

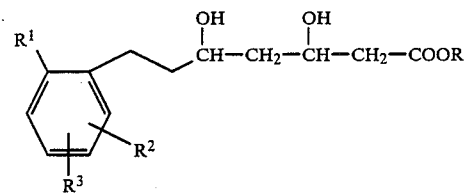
(V)

in which R, $R^1$, $R^2$ and $R^3$ have the same meanings as in general formula (IV).

The carboxylic acid ester function is saponified under alkaline conditions in the usual way, the free 3,5-dihydroxycarboxylic acid being isolated by acidification.

By heating in an inert solvent, for example benzene or toluene, this is cyclised to give the lactone (Ia), wherein E is a —CH=CH— radical, which, after hydrogenation by conventional processes, can be converted into a —CH$_2$—CH$_2$— bridge.

The starting materials can be prepared by the two schemes A and B shown in the following:

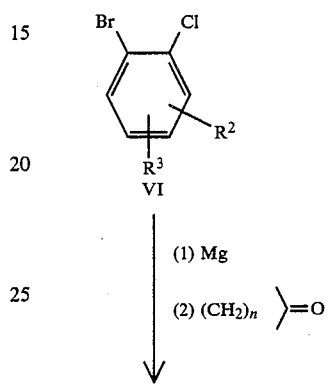
VI (1) Mg (2) (CH$_2$)$_n$ >=O

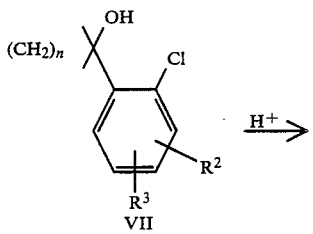
VII

H$^+$ →

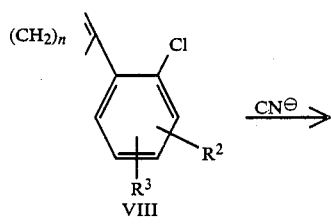
VIII

CN$^\ominus$ →

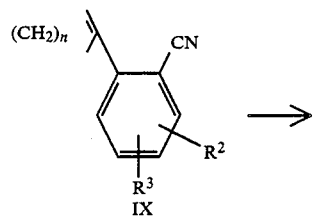
IX

→

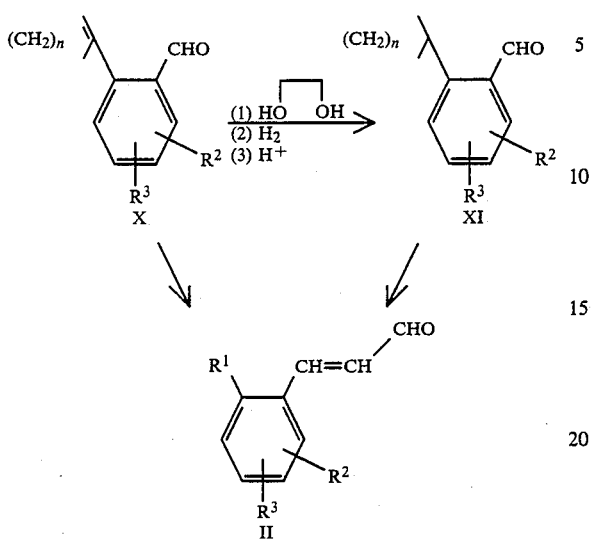

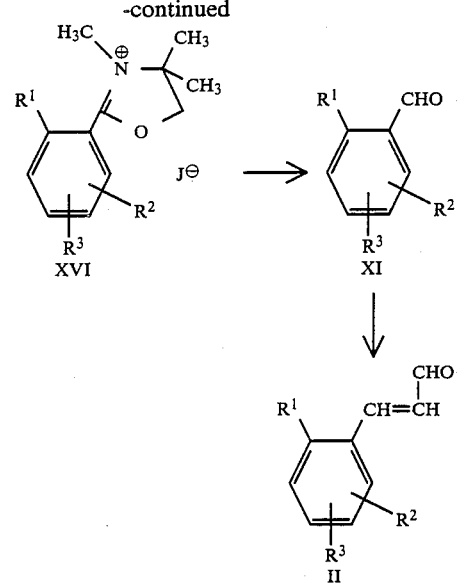

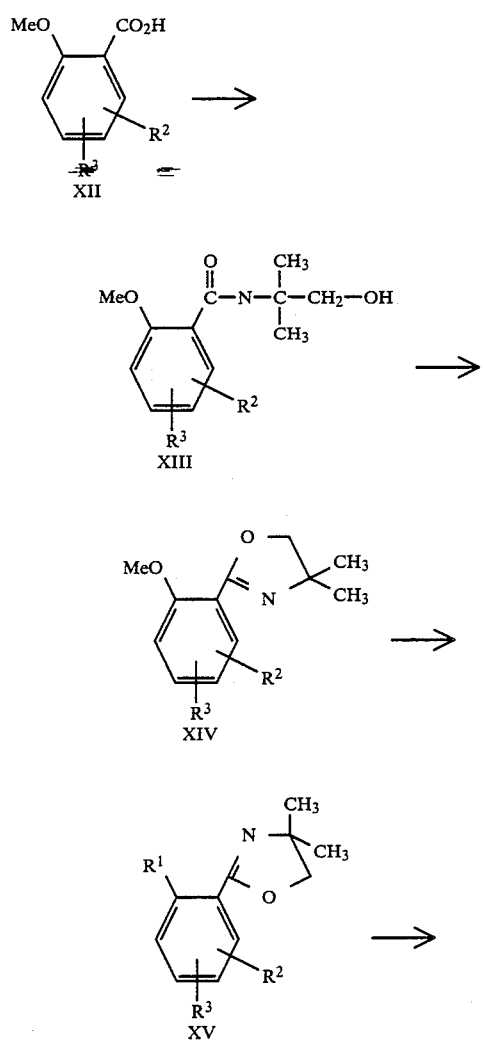

The compounds (Ia) and (Ib) according to the present invention are obtained from the cinnamaldehyde derivatives (II) prepared according to route A, wherein $R^1$, $R^2$ and $R^3$ have the above-given meanings.

The Grignard product of the o-chlorobromobenzene compound (VI) is reacted with a cycloalkanone in anhydrous diethyl ether or some other appropriate solvent, for example a higher ether, such as dibutyl ether or tetrahydrofuran, to give the corresponding cycloalkanol derivative (VII).

Dehydration to the corresponding cycloalkene takes place in an aqueous acid, for example formic acid, under reflux conditions.

The reaction to give the benzonitrile derivative (IX) takes place with the use of a cyanide salt, for example copper cyanide, in pyridine at an elevated temperature (according to W. E. Parham et al., J.A.C.S., 83, 1751/1961).

The nitrile is reduced with a complex metal hydride, for example DIBAH, in anhydrous diethyl ether or tetrahydrofuran as solvent, to give the benzaldehyde derivative (X).

By protection of the aldehyde function as a diacetal or cycloacetal, for example with ethyleneglycol, hydration by noble metal catalysis and splitting off of the protective groups, there can be obtained the phenylcycloalkyl system (XI) in a manner known from the literature.

Chain-lengthening to give the $\alpha,\beta$-unsaturated aldehyde (II) can be carried out, for example, by reacting the benzaldehyde derivatives (X) and (XI) with a phosphonium ylide (G. Wittig and R. Haag, Chem. Ber., 88, 1654/1955), this preferably being carried out in a polar aprotic solvent, for example tetrahydrofuran or dimethylformamide, with lithium methylate or butyl lithium as base, practically pure (E)-aldehydes thereby being obtained. The C-2 elongation can also be carried out with diethyl 2-(cyclohexylamino)-vinyl phosphonate (W. Nagata et al., Org. Synthesis, 53, 44/1973) in a manner known from the literature (W. Nagata and Y. Hayase, Tetrahedron Lett., 4359/1968 and J. Chem. Soc., C., 460/1969).

The direct aldol condensation also takes place by reacting the benzaldehyde derivative with the anion of an N-substituted ethylideneamine, for example ethylidenecyclohexylamine. The reaction, which is preferably carried out in the cold in an aprotic solvent, for example tetrahydrofuran, provides a β-hydroxy-β-phenylpropylideneamine which, with simultaneous dehydration and imine hydrolysis in an acidic medium, for example in dilute hydrochloric acid, gives the corresponding cinnamaldehyde (G. Wittig and A. Hesse, Org. Synth., 50, 67).

An alternative synthesis route (route B) is based on the work of Meyers (A. I. Meyers et al., J. Org. Chem., 43, 1372/1978), the key reaction of this variant being the exchange of a methoxy radical or fluorine atom by a Grignard compound.

For this purpose, the 2-methoxybenzoic acid derivative (XII) is reacted with thionyl chloride to give the corresponding acid chloride which is converted with 2-amino-2-methylpropanol into an amide (XIII), $R^2$ and $R^3$ having the same meanings as in general formula (I).

The benzamide (XIII) can be converted with thionyl chloride/diethyl ether to the oxazoline hydrochloride from which, after neutralisation with an aqueous alkali metal hydroxide solution, the oxazoline (XIV) can be isolated.

The reaction with a Grignard compound of a cycloalkyl halide in a solvent, for example diethyl ether or tetrahydrofuran, gives the arylcycloalkyl derivative (XV) (A. I. Meyers, R. Gabel and E. Mihelich, J. Org. Chem., 43, 1372/1978). Experiments with the corresponding fluorine derivative give the same desired compound.

Quaternisation with methyl iodide in nitromethane to give (XVI) and subsequent reduction with a mild reducing agent, for example sodium borohydride, in a lower alcohol and preferably in ethanol, and hydrolysis with an aqueous acid give the desired aldehyde (XI) in satisfactory yields.

The chain lengthening to give the α,β-unsaturated aldehyde corresponds to the methods described in route A.

The reaction of the unsaturated aldehydes (II) with the dianion of an acetoacetic acid ester (III) (for example analogously to S. N. Huckin and L. Weiler, Tetrahedron Lett., 4835/1971) in an appropriate aprotic solvent, for example diethyl ether or tetrahydrofuran, gives the 5-hydroxy-3-oxoheptenoic acid ester (IV).

The 3-oxo function of the ester (IV) can be converted with a mild reducing agent into the 3,5-dihydroxyheptenoic acid derivative (V), the reduction of (IV) thereby preferably being carried out with sodium borohydride in methanol as solvent. A stereospecific, stereo-selective reduction is achieved with a combination of a trialkylborane and sodium borohydride in tetrahydrofuran/methanol at a low temperature ($-78°$ C.) (cf. J. E. Lynch et al., Tetrahedron Lett., 28, 1385–1388/1987).

The carboxylic acid ester group of the compound (V) is saponified in the usual way by means of an alkali metal hydroxide to give, by acidification of the alkaline solution, the free dihydroxycarboxylic acid (Ib) (Z=H).

The resultant carboxylic acids can either be converted by conventional methods into pharmaceutically effective salts or cyclised to give the lactones (Ia) by heating in an inert solvent, for example benzene or toluene, with the splitting off of water.

The compounds according to the present invention of general formula (I), wherein $R^1$, $R^2$ and $R^3$ have the meanings given for (I) and E is the aryl lactone bridge (E) —CH=CH—, can be hydrogenated according to conventional methods, advantageously at ambient temperature, with hydrogen in the presence of a noble metal catalyst, for example platinum, in a solvent, such as methanol, tetrahydrofuran or ethyl acetate, to give compounds with a saturated $C_2$ bridge Apart from the compounds described in the following Examples, preferred compounds according to the present invention include the following:

E-6-[2-(2-cyclopent-1-enyl)-phenylethenyl]-4-hydroxy-3,4,5,6-tetrahydro-2H-pyran-2-one E-6-[2-(2-cyclopentyl)-phenylethenyl]-4-hydroxy-3,4,5,6-tetrahydro-2H-pyran-2-one E-6-[2-(2-cyclohex-1-enyl)-phenylethenyl]-4-hydroxy-3,4,5,6-tetrahydro-2H-pyran-2-one E-6-[2-(2-cyclohexyl)-phenylethenyl]-4-hydroxy-3,4,5,6-tetrahydro-2H-pyran-2-one E-6-[2-(2-cyclohexyl)-6-chlorophenylethyl]-4-hydroxy-3,4,5,6-tetrahydro-2H-pyran-2-one E-6-[2-(2-cyclohexyl)-4,6-dichlorophenylethyl]-4-hydroxy-3,4,5,6-tetrahydro-2H-pyran-2-one E-6-[2-(2-cyclohept-1-enyl)-phenylethenyl]-4-hydroxy-3,4,5,6-tetrahydro-2H-pyran-2-one E-6-[2-(2-cycloheptyl)-phenylethenyl]-4-hydroxy-3,4,5,6-tetrahydro-2H-pyran-2-one E-6-[2-(2-cycloheptyl)-6-chlorophenylethenyl]-4-hydroxy-3,4,5,6-tetrahydro-2H-pyran-2-one E-6-[2-(2-cycloheptyl)-4,6-dichlorophenylethenyl]-4-hydroxy-3,4,5,6-tetrahydro-2H-pyran-2-one E-6-[2-(2-cyclododec-1-enyl)-phenylethenyl]-4-hydroxy-3,4,5,6-tetrahydro-2H-pyran-2-one E-6-[2-(2-$C_{3,5}$-dimethylcyclohexyl)-phenylethenyl]-4-hydroxy-3,4,5,6-tetrahydro-2H-pyran-2-one E-6-[2-(2-cyclohexyl)-6-methylphenylethenyl]-4-hydroxy-3,4,5,6-tetrahydro-2H-pyran-2-one E-6-[2-(2-cycloheptyl)-4,6-dimethylphenylethenyl]-4-hydroxy-3,4,5,6-tetrahydro-2H-pyran-2-one E-6-[2-(2-cyclohexyl)-6-(2-methylethyl)-phenylethenyl]-4-hydroxy-3,4,5,6-tetrahydro-2H-pyran-2-one E-6-["(2-cyclohexyl)-4,6-dimethylphenylethenyl)-4-hydroxy-3,4,5,6-tetrahydro-2H-pyran-2-one.

BIOLOGICAL TEST SYSTEMS

Inhibition of HMG-CoA reductase in a microsome fraction from rat liver

For the determination of the HMG-CoA reductase activity, microsomes from rat livers, which had been treated for 7 days in the case of reversed day/night rhythm with cholestyramine, were separated by centrifuging. The action of the test compounds at a concentration of $10^{-4}$ M or $10^{-5}$ M on the formation of mevalonate from (S,R) $^{14}$C—HMG—CoA was investigated. The experimental conditions are described in detail by J. Huber. S. Latzien and B. Hamprecht, Hoppe-Seylers Z. Physiol. Chem., 354, 1654/1973.

$^{14}$C-acetate incorporation into cholesterol in rat hepatocyte monolayer cultures The influence of the test compounds at a concentration of $10^{-5}$ M on the $^{14}$C incorporation into cholesterol was investigated in rat hepatocyte monolayer cultures. The separation of the newly formed cholesterol took place by means of column extraction. Conditions for the culture and extraction are described by Pill et al., Fresenius Z. Anal. Chem., 327, 558–560/1987.

The results are shown in table I:

TABLE I

| Compound of Example | $^{14}$C-acetate incorporation in % | HMG-CoA-reductase Inhibition in % |
|---|---|---|
| Ex. 2 (a) | 59 | 95 |
| 2 (b) | 47 | 93 |
| 2 (c) | 36 | 90 |
| 2 (i) | 30 | 63 ($10^{-4}$ M) |

The compounds of general formulae (Ia) and (Ib) are characterised by a strong inhibition of HMG-CoA reductase. 3-Hydroxy-3-methylglutaryl coenzyme A (HMG-CoA) reductase is the strongest rate-determining enzyme in the biosynthesis of cholesterol (H. B. Zafarul and H. B. Brewer jr., Current Topics in Cellular Regulation, 20, 139–184/1981) and catalyses the synthesis of mevalonate from HMG-CoA. The inhibition of this enzyme results in a distinct lowering of the serum cholesterol (D. R. Illingworth and G. J. Sexton, Clin. Invest., 74, 1972–1978/1984). The combination with antihyperlipidaemics with different working mechanisms, for example bile acid-binding anion exchanger resins or fibrates, results in a further lowering of the serum cholesterol (G. L. Vega, S. M. Grundy, J.A.M.A., 257, 33–38/1987). In the case of severe forms of hypercholesterolaemia, this is necessary in order to achieve a sufficient serum cholesterol lowering.

The compounds according to the present invention are inhibitors of HMG-CoA reductase. Therefore, they can be used alone or in combination with other antihyperlipidaemics for the prophylaxis and therapy of diseases which are caused by increased serum cholesterol, for example coronary heart diseases, atheroscleroses, hypercholesterolaemia, hyperlipoproteinaemia and similar diseases.

Therefore, the present invention also provides pharmaceutical compositions based on compounds (Ia) or the corresponding dihydroxycarboxylic acids (Ib) or the salts and esters thereof and is further concerned with the use of these compounds as medicaments, especially for the treatment of hypercholesterolaemia.

The compounds of general formulae (Ia) and (Ib) are administered in various forms of administration, preferably orally in the form of tablets, capsules or liquids. The daily dose varies, according to body weight and constitution of the patients, in the range of from 2 to 2000 mg. but preferably in the dose range of from 20 to 500 mg.

The compounds according to the present invention can be used as lactones of general formula (Ia), in the form of free acids (Ib) (Z=H) or in the form of pharmaceutically acceptable salts or esters, namely, dissolved or suspended in pharmaceutically acceptable organic solvents, for example mono- or polyhydroxy alcohols, such as ethanol, glycerol or triacetin, in oils, for example sunflower oil, ethers or polyethers or also in the presence of pharmaceutically acceptable polymeric carriers, for example polyvinylpyrrolidinone, or other pharmaceutically acceptable additives, such as starch, cyclodextrin or polysaccharides.

The compounds according to the present invention can also be combined with additives which bind bile acids, especially non-toxic, basic exchanger resins which bind bile acids in a non-resorbable form in the gastro-intestinal tract, for example cholestyramine, or compounds disclosed in published European patent application No. A-0,157,410.

Preparation of the precursors according to Variant A o-(1-Cyclohexenyl)-chlorobenzene 25.7 g. (1.06 mol) magnesium turnings were reacted with 191.5 g. (1 mol) o-chlorobromobenzene in 500 ml. anhydrous diethyl ether to give the Grignard compound. 98.4 g. (1 mol) Cyclohexanone in 150 ml. anhydrous tetrahydrofuran were added dropwise thereto in the course of 45 minutes at 35° C., the reaction mixture was heated to reflux temperature for 90 minutes, cooled and decomposed with 130 ml. saturated aqueous ammonium chloride solution. The precipitate was filtered off with suction, washed with tetrahydrofuran and the organic phases dried and evaporated. The cyclohexanol derivative is obtained in quantitative crude yield (195 g.).

The alcohol was heated under reflux for 1.5 hours with 200 ml. 90% formic acid. After leaving to stand overnight, neutralisation was carried out with potassium hydroxide, the oil obtained was separated off, the aqueous phase was extracted with ligroin, combined with the oil, dried over anhydrous magnesium sulphate, evaporated and fractionally distilled. Yield 62% of theory; b.p. 74–75° C./0.1 mm.Hg; $n_D^{25}=1.560$.

o-(1-Cyclohexenyl)-benzonitrile

A mixture of 19.3 g. (0.1 mol) o-(1-cyclohexenyl)-chlorobenzene and 16.4 g. (0.18 mol) cuprous cyanide in 100 ml. N-methylpyrrolidinone was heated to 200° C. for 15 hours. For working up, the brown-black product was introduced into a solution of 40 g. ferric chloride, 10 ml. concentrated hydrochloric acid and 60 ml. water and the mixture heated for 0.5 hours to 60° to 70° C. The N-methylpyrrolidinone phase was separated off and the aqueous phase was extracted several times with toluene. The combined organic phases were successively washed with 2N hydrochloric acid, water and 10% aqueous sodium hydroxide solution and subsequently dried with anhydrous sodium sulphate and evaporated. Fractional distillation gave the desired benzonitrile derivative. Yield 68% of theory; b.p. 90–92° C./0.1 mm.Hg; $n_D^{26}=1.5648$.

o-(1-Cyclohexenyl)-benzaldehyde 360 ml. (0.36 mol) 1M DIBAH solution in methylene chloride was added dropwise in the course of 1.5 hours, while cooling to −15° to −10° C., into a solution of 60.5 g. (0.33 mol) o-(1-cyclohexenyl)-benzonitrile in 500 ml. anhydrous diethyl ether, stirred for a further hour at 0° C., subsequently for 3 hours at ambient temperature and decomposed with 5N sulphuric acid. The precipitate obtained was filtered off with suction and the organic phase was washed with an aqueous solution of sodium chloride, dried and evaporated. The aldehyde obtained was used for the following stage without further purification (crude yield 95% of theory). NMR,(60 MHz, CDCl$_3$, ppm): 10.25 (1H, s, —CHO); 6.90–8.10 (4H, m. aromat. protons); 5.70 (1H, m, olef. proton); 1.05–2.50 (8H, m, cyclohexenyl radical).

o-(1-Cyclohexyl)-benzaldehyde 16.3 g. (0.1 mol) o-(1-Cyclohexenyl)-benzaldehyde were heated for 4 hours in a Dean and Stark apparatus with 6.85 g. (0.11 mol) ethyleneglycol and 1 g. p-toluenesulphonic acid in 400 ml. toluene. Thereafter, the calculated amount of water had separated off. The isolated protected aldehyde was taken up in ethanol and hydrogenated over platinum oxide as catalyst. After filtering and evaporating off the solvent, the crude product was taken up in 300 ml. dioxan, mixed with 80 ml. of a 10% aqueous solution of oxalic acid and heated under reflux for 2 hours. After extraction with ethyl acetate, the organic phase was washed with water, dried over anhydrous magnesium sulphate and evaporated. Flash chromatography (hexane/ethyl acetate 5:1 v/v) gave the aldehyde in pure form in a yield of 65% of theory.

NMR (60 MHz, CDCl$_3$, ppm): 10.28 (1H, s, —CHO); 7.01–7.80 (4H, m, arom. protons); 1.05–3.10 (11H, m, cyclohexyl).

o-(Cyclohexyl)-cinnamaldehyde 35 ml. (0.05 mol) butyl lithium in hexane were added at 0° C. to a solution of 7 ml. (5 g., 0.05 mol) diisopropylamine in 250 ml. anhydrous tetrahydrofuran. Thereafter, 6.25 g. (0.05 mol) ethylidenecyclohexylamine were added thereto at the same temperature and the reaction mixture further stirred for 15 minutes. After cooling to −78° C., 9.4 g. (0.05 mol) o-(cyclohexyl)-benzaldehyde in 75 ml. tetrahydrofuran were added dropwise thereto, followed by warming to ambient temperature within the course of 3 hours. The reaction mixture was decomposed with water, extracted with diethyl ether and the organic phase dried and evaporated. The imine obtained in quantitative crude yield was dissolved with 19 g. (0.15 mol) oxalic acid in 160 ml. tetrahydrofuran and 35 ml. water and heated under reflux for 30 minutes. After mixing with water, extraction was carried out with diethyl ether and the organic phase dried and evaporated. The cinnamaldehyde was purified by flash chromatography with heptane/ethyl acetate (5:1 v/v) as elution agent mixture.

NMR (60 MHz, CDCl$_3$, ppm): 9.85 (d, 1H, CHO, J=8 Hz); 7.05–7.70 (m, 4H, arom. protons); 7.95 (d, 1H, J=16 Hz, CH=CH—CHO); 6.75 (dd, 1H, 8 Hz and 16 Hz, CH=CH—CHO); 1.05–2.10 and 2.90 (m, 11H, cyclohexyl protons).

The following Examples are given for the purpose of illustrating the present invention:

EXAMPLE 1

Synthesis of (E)-6-[2-(2-cycloheptyl)-4,6-dichlorophenylethenyl]-4-hydroxy-3,4,5,6-tetrahydro-2H-pyran-2-one Variant B 2,4-Dichloro-6-methoxybenzoic acid chloride.

26.0 g. (0.117 mol) 2,4-Dichloro-6-methoxybenzoic acid were dissolved in 50 ml. anhydrous methylene chloride and, after the addition of 0.1 g. dimethylaminopyridine, 50 ml. thionyl chloride were added dropwise thereto at ambient temperature. After stirring for 15 hours, the reaction mixture was evaporated and the residue distilled. Yield: 55% of theory; b.p. 118–124° C./0.1 mm.Hg.

N-(2-Hydroxy-1,1-dimethylethyl)-2,4-dichloro-6-methoxy-benzamide.

13.9 g. (0.058 mol) of the above-mentioned benzoic acid chloride derivative were dissolved in 50 ml. anhydrous methylene chloride and a solution of 11.1 ml. (0.116 mol) 2-amino-2-methyl-1-propanol added dropwise thereto at 0° C. After 1 hour at ambient temperature, the mixture was filtered, the filtrate was washed with water, 5% hydrochloric acid, 5% aqueous sodium hydroxide solution and with a concentrated solution of sodium chloride and evaporated. Yield 90% of theory.

2-(2,4-Dichloro-6-methoxyphenyl)-4,5-dihydro-4,4-dimethyloxazole.

10 ml. Thionyl chloride were added dropwise to 2.0 g. (6.8 mol) of the benzamide, while cooling with ice. Subsequently, a spatula tip of DMAP was added thereto. After stirring for 2 hours at ambient temperature, anhydrous diethyl ether was added thereto, the mixture thereafter briefly stirred and the oxazoline hydrochloride filtered off. The desired compound was extracted with diethyl ether after neutralisation with a dilute aqueous solution of sodium hydroxide and the organic phase was dried and evaporated. Yield 87% of theory; m.p. 45° C.

2-(3,5-Dichloro-6-cycloheptylphenyl)-4,5-dihydro-4,4-dimethyloxazole.

15.05 g. (55 mmol) of the above-mentioned oxazole derivative were dissolved in 100 ml. anhydrous tetrahydrofuran and mixed at ambient temperature with a 2M Grignard solution (75 mmol) in tetrahydrofuran (prepared from bromocycloheptane and activated magnesium turnings). After stirring for 20 hours at 20° C., a further 60 mmol of Grignard solution were added dropwise thereto and the reaction mixture warmed to 40° C. for 20 hours. After cooling to 5° C., the mixture was mixed with a saturated aqueous solution of ammonium chloride, extracted with diethyl ether and the organic phase dried and evaporated (almost quantitative crude yield).

NMR (60 MHz, CDCl$_3$, ppm): 1.30 (6H, s); 3.87 (2H, s); 7.07–7.30 (2H, m).

2-(3,5-Dichloro-6-cycloheptylphenyl)-4,5-dihydro-3,4,4-trimethyloxazolium iodide.

4.7 ml. (10.65 g., 75 mmol) methyl iodide were added to 17 g. (50 mmol) of the oxazole derivative in 75 ml. nitromethane and heated for 10 hours to 100° C. After evaporation in a vacuum, the residue remaining behind was washed with a little diethyl ether and filtered off with suction. The oxazolium iodide derivative was used for the next reaction without further purification. Yield 78% of theory; m.p. 145° C. (decomp.).

2,4-Dichloro-6-cycloheptylbenzaldehyde.

2.5 g. (65 mmol) sodium borohydride were added portionwise to a suspension of 17.2 g. (45 mmol) of the oxazolium iodide derivative in 175 ml. anhydrous ethanol, followed by stirring for 3 hours at ambient temperature. After mixing with 300 ml. 2N hydrochloric acid, the reaction mixture was heated to 80° C. for 1 hour, cooled, diluted with water and extracted several times with diethyl ether. The organic phases were washed with a concentrated aqueous solution of sodium chloride and water, dried and evaporated. The aldehyde could be obtained in pure form after flash chromatography (hexane/ethyl acetate 8:1 v/v). Yield 56% of theory.

NMR (60 MHz, CDCl$_3$, ppm): 10.52 (1H, s CHO); 7.05–7.40 (2H, m).

2,4-Dichloro-6-cycloheptylcinnamaldehyde.

5.2 g. (20 mmol) Diethyl-2-(cyclohexylamino)-vinyl phosphonate (W. Nagata et al., Org. Synthesis, 53, 44/1973) were added to a suspension of 0.48 g. (20 mmol) sodium hydride in 30 ml. anhydrous tetrahydrofuran at 0° C. At the same temperature, 30 minutes later a solution of 4.6 g. (17 mmol) of the 2,4-dichloro-6-cycloheptylbenzaldehyde in 30 ml. anhydrous tetrahydrofuran were run in. The temperature thereby increased from 0° C. to 30° C. The reaction mixture was further stirred for 3 hours, poured on to ice water and extracted with diethyl ether. The residue obtained after evaporation of the ethereal phase was dissolved in 100 ml. tetrahydrofuran, 6 g. oxalic acid in 100 ml. water were added thereto and the reaction mixture heated to reflux temperature for 1.5 hours. The tetrahydrofuran was distilled off in a vacuum and the aqueous phase extracted with ethyl acetate. The organic phase was successively washed with 2N hydrochloric acid, water, aqueous bicarbonate solution and water and then dried and evaporated. Purification took place by flash chromatography (hexane/ethyl acetate 5:1 v/v); m.p. 90°–92° C.

NMR (60 MHz, CDCl$_3$, ppm): 10.85 (1H, d, CHO, J=8 Hz); 7.65 (1H, d, CH=CH—CHO, J =15 Hz); 6.48 (1H, dd, CH=CH—CHO, J=15 Hz, J=8 Hz). Methyl (E)-7-(2,4-dichloro-6-cycloheptylphenyl)-5-hydroxy-3-oxo-6-heptenoate.

0.9 ml. (8 mmol) Methyl acetoacetate was added dropwise at 0° C. to a suspension of 0.31 g. (13 mmol) sodium hydride in 30 ml. anhydrous tetrahydrofuran. After stirring for 15 minutes, 7.5 ml. (13 mmol) of a 1.7 molar solution of butyl lithium in hexane were added thereto in the course of 30 minutes. To the resultant yellow solution were added 2.4 g. (8 mmol) 2,4-dichloro-6-cycloheptylcinnamaldehyde in 20 ml. anhydrous tetrahydrofuran, the reaction mixture was then stirred for 1 hour at 0° C. and subsequently decomposed with 50 ml. semi-concentrated hydrochloric acid. The reaction mixture was diluted with water, extracted with diethyl ether and the ethereal extracts washed neutral, dried and evaporated. The crude product was purified by flash chromatography (heptane/ethyl acetate 3:1 v/v). Yield 68% of theory; m.p. 78°–79° C.

NMR (300 MHz, d$_6$-DMSO, ppm): 1.40–1.80 (m, 12H, cycloheptyl radical); 2.75 (d, J=6 Hz); 3.00 (1H, m); 3.23 (s, 1H); 3.62 (s, 3H); 4.6 (m, 1H); 5.78 (1H, dd, J=15 and 6 Hz); 6.48 (1H, d, J=15 Hz); 7.24 and 7.36 (2H, 2d, J=2 Hz).
Methyl (E)-7-(2,4-dichloro-6-cycloheptylphenyl)-3,5-dihydroxy-6-heptenoate.

To 0.8 g. (2 mmol) of the above-described 3-keto ester in 15 ml. anhydrous methanol were added portionwise at 0° C. 100 mg. sodium borohydride, the solution was stirred for 2 hours with further cooling, decomposed with 6N hydrochloric acid, extracted with diethyl ether and the organic phase was dried and evaporated. Yield 87% of theory.

(E)-6-[2-(2-Cycloheptyl)-4,6-dichlorophenylethenyl]-4-hydroxy-3,4,5,6-tetrahydro-2H-pyran-2-one.

To a solution of 0.65 g. (1.5 mmol) of the abovedescribed dihydroxy ester in 20 ml. ethanol were added 3 ml. (3 mmol) of a 1M aqueous solution of sodium hydroxide, followed by stirring for 2 hours at ambient temperature. After acidification with dilute hydrochloric acid, extraction was carried out with diethyl ether and the ethereal phase was dried and evaporated. The residue was dissolved in 30 ml. toluene and stirred for 12 hours at 60° C. in order completely to cyclise the dihydroxycarboxylic acid to the lactone. The mixture of trans- and cis-lactone (ratio 2:1) was completely separated by flash chromatography (elution agent methylene chloride/acetone 20:1 v/v).

(±)-trans isomer.

NMR (300 MHz, DMSO, ppm): 7.40 and 7.29 (2H, 2d, J=2 Hz); 6.62 (1H, d, J=15 H); 5.85 (1H, dd, J=15 and 8 Hz); 5.32 (1H, m); 5.24 (1H, d, J=3 Hz, OH); 4.20 (1H, m); 2.95 (1H, m); 2.72 (1H, dd, J=16 and 6 Hz); 2.40–2.55 (1H, m); 1.4–2.02 (14H, m).

The characterisation of the cis and trans isomers took place via NMR spectroscopy.

(±)-cis isomer.

NMR (300 MHz, DMSO, ppm): 7.39 and 7.28 (2H, 2d, J=2 Hz); 6.60 (1H, d, J=15 Hz); 5.82 (1H, dd, J=15 and 8 Hz); 5.15 (1H, d, J=3 Hz, OH); 5.02 (1H, m); 4.20 (1H, m); 2.95 (1H, m); 2.85 (1H, dd, J=16 and 6 Hz); 2.32 (1H, dd, J=16 and 4 Hz); 1.4–1.85 (14H, m).

The detection of the ± trans and cis isomers took place in the usual way with optically-active bases.

Example 2

The following ± trans compounds were obtained in a manner analogous to that described in Example 1:

TABLE 1

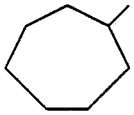

| | R$_1$ | R$_2$ | R$_3$ | E | m.p. °C. | Olefin. Prot. (E bridge) | H$_a$ | H$_b$ | OH |
|---|---|---|---|---|---|---|---|---|---|
| (a) |  | Cl | Cl | —CH=CH— | oil | 6.61 (i, J=15Hz) 5.85 (dd, J=15 u.6 Hz) | 5.25–5.35 | 4.15–4.23 | 5.25 (d, J=3Hz) |
| (b) |  | Cl | H | —CH=CH— | oil | 6.65 (d, J=16Hz) 5.81 (dd, J=16 u.6 Hz) | 5.28–5.37 | 4.15–4.25 | 5.24 (d, J=3Hz) |

TABLE 1-continued

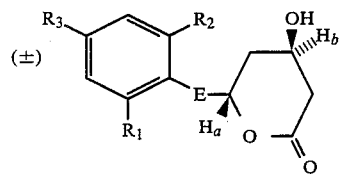

| | $R_1$ | $R_2$ | $R_3$ | E | m.p. °C. | Olefin. Prot. (E bridge) | $H_a$ | $H_b$ | OH |
|---|---|---|---|---|---|---|---|---|---|
| (c) | cyclohexyl | Cl | Cl | —CH=CH— | 103–104 | 6.60 (d, J=16Hz) 5.88 (dd, J=16 u.8 Hz) | 5.25–5.35 (m) | 4.16–4.23 | — |
| (d) | cyclohexyl | Cl | H | —CH=CH— | 90–92 | 6.65 (d, J=16Hz) 5.82 (dd, J=16 u.8 Hz) | 5.24–5.34 | 4.18–4.24 | — |
| (e) | cyclopentyl | H | H | —CH=CH— | oil | 7.04 (d, J=16Hz) 6.15 (dd, J=16 u.7 Hz) | 5.25–5.34 (m) | 4.15–4.23 (m) | 5.22 (broad) |
| (f) | cyclopentyl | H | H | —CH₂CH₂— | oil | — | 4.55–4.65 (m) | 4.10–4.16 | 5.10 (broad) |
| (g) | methylcyclohexyl | H | H | —CH=CH— | oil | 7.00 (d, J=16Hz) 6.15 (dd, J=16 u.7 Hz) | 5.25–5.35 (m) | 4.14–4.21 (m) | 5.21 J=3Hz |
| (h) | cyclohexyl | H | H | —CH₂CH₂— | oil | — | 4.54–4.64 (m) | 4.10–4.16 (m) | 5.11 J=3Hz |
| (i) | cyclohexenyl | H | H | —CH=CH— | oil | 6.81 (d, J=16Hz) 6.10 (dd, J=16 u.8 Hz) | 5.25–5.35 (m) | 4.34–4.41 (m) | — |
| (j) | cycloheptyl | H | H | —CH=CH— | oil | 6.98 (d, J=16Hz) 6.13 (dd, J=16 u.8 Hz) | 5.25–5.30 (m) | 4.14–4.22 (m) | 5.20 (d, J=3Hz) |
| (k) | macrocyclic (CH=CH, (CH₂)₁₀) | H | H | —CH=CH— | oil | 6.82 (d, J=16Hz) 6.20 (dd, J=16 u.8 Hz) | 5.15–5.25 (m) | 4.10–4.21 (m) | 5.12 (d, J=3Hz) |
| (l) | macrocyclic (CH₂, CH₂, (CH₂)₁₀) | H | H | —H₂C—CH₂— | oil | — | 4.58–4.67 | 4.10–4.17 | 5.14 (d, J=2Hz) |
| (m) | cyclohexyl | CH₃ | H | —CH=CH— | oil | 6.68 (d, J=16Hz) 5.66 (dd, J=16 u.6.5 Hz) | 5.27–5.35 | 4.20 | 5.24 (d, J=3Hz) |

TABLE 1-continued

|   | R₁ | R₂ | R₃ | E | m.p. °C. | Olefin. Prot. (E bridge) | $H_a$ | $H_b$ | OH |
|---|---|---|---|---|---|---|---|---|---|
| (n) | cycloheptyl | CH₃ | CH₃ | —CH=CH— | 114–115° C. | 6.65 (d, J=16Hz) 5.62 (dd, J=16 u.6.5 Hz) | 5.22–5.32 | 4.19 | 5.25 (broad) |
| (o) | 4-isopropylcyclohexyl | H₃C—CH— H₃C | H | —CH=CH— | 102–104° C. | 6.82 (d, J=16Hz) 5.63 (dd, J=16 u.6 Hz) | 5.38–5.48 | 4.45 | — |
| (p) | cyclohexyl | CH₃ | CH₃ | —CH=CH— | 129–131° C. | 6.65 (d,J=16Hz) 5.63 (dd,J=16 u.6.5 Hz) | 5.23–5.32 | 4.18 | 5.25 (broad) |

We claim:

1. Compounds of the formula:

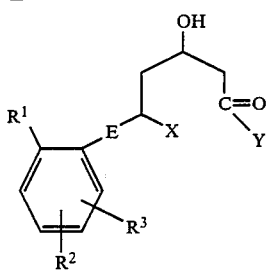

wherein:
E is —CH₂—CH₂— or —CH=CH—
$R^1$ is a saturated or ethylenically unsaturated cycloaliphatic hydrocarbon containing 5 to 12 carbon atoms containing up to 4 substituents, which may be the same or different, and are each selected from alkyl of up to 6 carbon atoms and halogen
$R^2$ and $R^3$ are the same or different and are each selected from cycloaliphatic hydrocarbons containing 3 to 7 carbon atoms, hydrogen, halogen, alkyl of up to 8 carbon atoms and alkoxy of up to 8 carbon atoms
X and Y taken together on —O—.

2. The compounds as claimed in claim 1, wherein $R^2$ is hydrogen, halogen, trifluoromethyl, alkyl of up to 4 carbon atoms or alkoxy of up to 4 carbon atoms.

3. The compounds as claimed in claim 1, wherein $R^3$ is hydrogen, halogen, trifluoromethyl, alkyl of up to 4 carbon atoms or alkoxy of up to 4 carbon atoms.

4. The compounds as claimed in claim 1, wherein said $R^1$ is selected from cyclopentyl, cyclohexyl, cycloheptyl, cyclododecyl, cyclopentenyl, cyclohexenyl, cycloheptenyl or cyclododecenyl.

5. The compounds as claimed in claim 1, wherein said $R^2$ and $R^3$ are respectively selected from cyclopropyl, cyclopentyl or cyclohexyl.

6. The compounds as claimed in claim 1, wherein said alkyl is selected from methyl, ethyl, propyl or butyl and said alkoxy is selected from methoxy or ethoxy.

7. The compounds claimed in claim 1, wherein said halogen is selected from fluorine, chlorine or bromine.

8. The compounds claimed in claim 1 comprising translactone ring stereoisomers having the absolute configuration 4R, 6S.

9. The compounds claimed in claim 1, wherien $R^1$ is cycloheptyl, $R^2$ and $R^3$ are chloro, E is —CH=CH—, and X and Y taken together are —O—.

10. The compounds claimed in claim 1, wherein $R^1$ is cycloheptyl, $R^2$ is chloro, $R^3$ is hydrogen, E is —CH=CH— and X and y taken together are —O—.

11. The compounds claimed in claim 1, wherein $R^1$ is cyclohexyl, $R^2$ and $R^3$ are each chloro, E is —CH=CH—, and X and Y taken together are —O—.

12. The compounds claimed in claim 1, wherein $R^1$ is cyclohexenyl, $R^2$ and $R^3$ are each hydrogen, E is —CH=CH— and X and Y taken together are —O—.

13. A composition comprising at least one compound as claimed in claim 1, in combination with a pharmaceutically acceptable carrier therefor.

14. The composition claimed in claim 13, wherein said carrier comprises an organic solvent, an oil suspending medium or a polymeric carrier.

15. The composition claimed in claim 14, wherein said organic solvent is selected from pharmaceutically acceptable proportions of ethanol, glycerol or triacetin.

16. The composition claimed in claim 14, wherein said oil comprises sunflower seed oil.

17. The composition claimed in claim 14, wherein said polymeric carrier comprises polyvinyl pyrrolidinone.

18. The composition claimed in claim 13, additionally containing at least one of starch, cyclodextrin and polysaccharides.

19. The composition claimed in claim 13, in the form of a tablet.

20. The composition claimed in claim 13, in the form of a capsule.

21. The composition claimed in claim 13, in the form of a liquid.

* * * * *

UNITED STATES PATENT AND TRADEMARK OFFICE
CERTIFICATE OF CORRECTION

PATENT NO. : 4,970,077

DATED : November 13, 1990

INVENTOR(S) : Bruno DRECKMANN et al.

It is certified that error appears in the above-identified patent and that said Letters Patent is hereby corrected as shown below:

On the title page, Item [21], "358,792" should read --359,792--.

Signed and Sealed this

Twenty-first Day of April, 1992

Attest:

HARRY F. MANBECK, JR.

Attesting Officer

Commissioner of Patents and Trademarks